United States Patent [19]
Panigrahi et al.

[11] Patent Number: 6,132,710
[45] Date of Patent: Oct. 17, 2000

[54] PREVENTING/TREATING NEONATAL NEC BY ADMINISTERING *LACTOBACILLUS SALIVARIUS* AND *LACTOBACILLUS PLANTARUM* OR A COMBINATION THEREOF

[75] Inventors: Pinaki Panigrahi, Laurel; Ira H. Gewolb, Pikesville; J. Glenn Morris, Jr., Baltimore, all of Md.

[73] Assignee: ProBiotix, Inc., Baltimore, Md.

[21] Appl. No.: 08/818,995

[22] Filed: Mar. 17, 1997

[51] Int. Cl.$^7$ .............................. A01N 63/00; C12N 1/00; C12N 1/20

[52] U.S. Cl. ................. 424/93.45; 424/93.3; 435/252.4; 435/252.9; 435/853; 435/857

[58] Field of Search ................................. 435/252.9, 853, 435/857, 252.4; 424/93.45, 93.3

[56] References Cited

U.S. PATENT DOCUMENTS

| | | | |
|---|---|---|---|
| 4,689,266 | 8/1987 | Eckler | 428/334 |
| 5,411,751 | 5/1995 | Crissinger et al. | 426/2 |
| 5,413,785 | 5/1995 | Nanji | 424/93.45 |
| 5,439,678 | 8/1995 | Dobrogosz et al. | 424/93.45 |

OTHER PUBLICATIONS

Zetterstrom et al., Early Infant Feeding . . . , Acta Paediatr Jpn, Oct. 1994, 36(5), 562–571.

Miller et al., Enteral Feeding of Premature . . . , Arch Dis Child, Nov. 1993, 69 (5 Spec No), 483–487.

Link–Amster et al., Modulation of a Specific . . . , FEMS Immunol Med Microbiol, Nov. 1994, 10 (1), 55–63.

Bernet et al., *Lactobacillus acidophilus* . . . , Gut, Apr. 1994, 35 (4), 483–489.

Hillman et al., The Effect of Mixtures . . . , Lett Appl Microbiol, Feb. 1995, 20 (2), 130–133.

Greene et al., Factors Involved in Adherence . . . , Appl Environ Microbiol, Dec. 1994, 60 (12), 4487–4494.

Bomba et al., Colonization of the Digestive . . . , Vet Med (Praha), 1994, 39 (11), 701–710.

Bomba et al., Interactions of Lactobacillus . . . , Vet Med (Praha), May 1996, 41 (5), 155–158.

*Primary Examiner*—David M. Naff
*Assistant Examiner*—Deborah K. Ware
*Attorney, Agent, or Firm*—James Creighton Wray; Meera P. Narasimhan

[57] ABSTRACT

Gastrointestinal tissue injury and infections are treated by orally administering Lactobacilli strains. The Lactobacilli strains prevent neonatal necrotizing enterocolitis tissue injury and necrotizing enterocolitis in preterm infants. Preterm infants, full-term infants, children and adults as well as animals may be given the Lactobacilli strains. The strains are *Lactobacillus salivarius* strain ATCC 202196 and *Lactobacillus plantarum* strain ATCC 202195. Further, the strains may be given individually or as a combination of the two strains. In addition, the strains are useful in treating diarrhea. The Lactobacilli strains normalize and balance bacterial milieu in the gastro-intestinal tract. The Lactobacilli strains may be in lyophilized capsule form. The capsule may be an enteric coated slow-release microcapsule. The Lactobacilli strains may also be administered by means of a naso-gastric tube, especially for preterm infants.

12 Claims, 2 Drawing Sheets

PREVENTING/TREATING NEONATAL NEC BY ADMINISTERING *LACTOBACILLUS SALIVARIUS* AND *LACTOBACILLUS PLANTARUM* OR A COMBINATION THEREOF

FIELD OF THE INVENTION

This invention describes two Lactobacillus strains isolated from human stools that have the unique property of blocking experimental Neonatal Necrotizing Enterocolitis (NEC).

BACKGROUND OF THE INVENTION

NEC is the most serious gastrointestinal disorder of premature infants and one of the leading causes of death in neonatal intensive care units (NICU). It is the most common surgical emergency in the newborn period and the second leading cause of morbidity and mortality in the preterm population. The incidence of NEC in selected studies has ranged from fewer than 1% to as many as 5% of NICU admissions (Stoll B J: Epidemiology of necrotizing enterocolitis. Clin Perinatol 21:205–218, 1994.)

A recent multicenter study of 2681 infants weighing 501–1500 grams reported that proven NEC (Bell Stage 2-3) occurred in 10.1% and suspected NEC (Bell Stage 1) in a further 17.2% of the cohort; mortality was 54% in infants with severe (Stage 3) NEC. These data indicate that NEC is a major public health problem in neonates: given the ~4 million births/year in the United States, NEC would be expected to develop in 1200–9600 infants, of whom between 9–28% will die as a result of their disease. (Walsh M C, Kleigman R M, Fanaroff A A: Necrotizing enterocolitis: A practitioner's perspective. Pediatr Rev 9:219–226, 1988; Uauy R D, Fanaroff A A, Korones S B, Phillips E A, Philips J B, Wright L: Necrotizing enterocolitis in very low birth weight infants: Biodemographic and clinical correlates. J Pediatr 119:630–38, 1991.)

Earlier studies indicated a mortality of 10–55% in premature infants (Stoll B J, Kanto W P, Glass R I, Nahmias A J, Brann A W: Epidemiology of necrotizing enterocolitis: A case control study. J Pediatr 96:447–451, 1980).

Survivors of NEC can also have considerable long-term morbidity resulting from their disease, including short-gut syndrome, failure-to-thrive, intestinal stricture, and the need for repeated surgery (Simon N P: Follow-up for infants with necrotizing enterocolitis. Clin Perinatol 21:411–424, 1994).

NEC is primarily a disease of premature infants who have survived the immediate neonatal period. There is an increased incidence of NEC with decreasing birthweight and gestational age; in a population-based study involving all infants born in a single state during a 1-year period, the incidence of NEC was 42.1/1000 livebirths weighing <1000 grams, compared with only 3.8/1000 in the 1500–2501 gm birthweight category, and 0.11/1000 in children weighing >2500 grams at birth (Wilson R, Canto W P, McCarthy B J et al.: Epidemiologic characteristics of necrotizing enterocolitis: a population based study. Am J Epidemiol 114:880–887, 1981.)

The recent introduction of replacement surfactant therapy has resulted in a decrease in the mortality rate associated with respiratory distress syndrome in extremely low-birthweight infants, precisely that population at highest risk for developing NEC. With the prevalence of NEC likely to rise, NEC may become an increasingly important cause of neonatal mortality in the 1990's.

All premature infants are at risk of developing NEC, with the risk increasing with decreasing gestational age. Of 4 million live births/yr in the U.S., approximately 8% (320,000) are prematurely born. All of these infants will be eligible to receive multiple doses of Lactobacillus/Bifidobacteria preparation. Currently the clinical management of NEC is largely empiric consisting of general supportive measures. Cost of the intensive medical care per patient with NEC ranges between $50,000–$100,000; with even higher hospital cost for those requiring surgery. In spite of all these interventions, mortality rate in NEC has been reported to be upto 55%.

In addition, those undergoing surgery are often left with long term dysfunctions such as short gut syndrome and failure to thrive, translating to continued morbidity and medical expense.

Stool Microfloral Colonization Patterns in the Newborn Period

Bacterial colonization of the neonatal gastrointestinal tract begins when maternal cervical and vaginal flora is encountered by the infant during delivery. (Brooke I, Barrett C T, Brinkman C R, Martin W J, Finegold S M: Aerobic and anaerobic bacterial flora of the maternal cervix and newborn gastric fluid and conjunctiva: A prospective study. Pediatrics 63:451–455, 1979).

By 10 days of age the large majority of healthy full-term newborns are fully colonized with a variety of bacterial species (Long S S, Swenson R M: Development of anaerobic fecal flora in healthy newborn infants. J Pediatr 91:298–301, 1977.)

In contrast, the gut of a premature infant, cared for in relatively aseptic NICU conditions and usually receiving antibiotics shortly after birth, does not get the opportunity for proper colonization by the normally heterogeneous bacterial flora and demonstrates delayed colonization with a limited number of bacterial species (Gupta S, Morris J G, Panigrahi P, Natero J P, Glass R I, Gewolb I H: Endemic necrotizing enterocolitis:lack of association with a specific infectious agent. Pediatr Infect Dis 13:725–734, 1994; Goldman D A, Leclair J, Macone A: Bacterial colonization of neonates admitted to an intensive care environment. J Pediatr 93: 288–93, 1978; Bennet R, Eriksson M, Nord C E, Zetterstrom R: Fecal bacterial microflora of newborn infants during intensive care management and treatment with five antibiotic regimens. Pediatr Infect Dis J 5:533–539, 1986).

Indeed, we have recently shown that the stool of preterm infants, with and without NEC, is colonized on the average by fewer than 2.5 species of aerobic bacteria, compared to >10 species in fullterms (Gupta S, Morris J G, Panigrahi P, Natero J P, Glass R I, Gewolb I H: Endemic necrotizing enterocolitis:lack of association with a specific infectious agent. Pediatr Infect Dis 13:725–734, 1994.)

Human milk populates the intestine with Bifidobacteria and Lactobacilli, generating a very different gut flora than that seen after formula feeding (Keyworth N, Miller M R, Holland K T: Development of cutaneous microflora in premature Neonates. Arch Dis Child 67:797, 1992; Yoshioka H, Iseki K, Fujita K: Development and differences of intestinal flora in the neonatal period in breast-fed and bottle-fed infants. Pediatrics 73:317–321, 1983.) It has long been known that Bifidobacteria are the most common organisms found in newborn fecal material. Yoshioka et al. used quantitative culture methods to study differences in intestinal colonization patterns in breast- and bottle-fed full term neonates. (Yoshioka H, Iseki K, Fujita K: Development and differences of intestinal flora in the neonatal period in breast-fed and bottle-fed infants. Pediatrics 73:317–321, 1983).

Both groups were first colonized with Enterobacteria. However, by day 6, Bifidobacteria exceeded Enterobacteria by 1000:1 in breast-fed infants; in bottle-fed infants, Enterobacteria outnumbered Bifidobacteria by 10:1. By one month of age, Bifidobacteria was the predominant species in both groups, but the absolute number of these organisms was 10 times fewer in bottle-fed babies compared to the breast-fed group.

Of interest, a recent study demonstrated a higher incidence of aerobic flora in preterm NICU infants fed frozen human milk, as well as an increased rate of isolation of S. epidermidis. (El-Mohandes A, Keiser J F, Johnson L A, Refat M, Jackson B J: Aerobes isolated in fecal microflora of infants in the intensive care nursery: Relationship to human milk use and systemic sepsis. Am J Infect Control 21:231–234, 1993.)

A number of investigators have found decreased numbers of Lactobacilli in preterm infants; this reduction was correlated with previous antibiotic therapy and time spent in an incubator (Hall M A, Cole C B, Smith S L, Fuller R, Rolles C J: Factors influencing the presence of faecal lactobacilli in early infancy. Arch Dis Child 65:185–188, 1990.)

Delayed transit time, seen in preterm infants could permit bacterial overgrowth that could, in turn, initiate the cascade of events that lead to NEC. This finding again underscores the potential for overgrowth by a small number of potential pathogens in the low birth weight infant in the NICU. (Vantrappen G, Janssens J, Choos Y: The interdigestive motor complex of normal subjects and patients with bacterial overgrowth of the small intestine. J Clin Invest 59:1158, 1977).

The experience with germ-free animals may be applicable to the situation existing in the preterm infant. If germ free animals are contaminated with a single strain of organism, that organism, even if not normally indigenous or pathogenic, can populate the gut in very high concentrations (Gibbons R J, Socransky S S, Kapsimalis B: Establishment of human indigenous bacteria in germ free mice. J Bacteriol 88:1316–1323, 1964; Schaedler R W, Dubos R, Costello R: Association of germ free mice with bacteria isolated from normal mice. J Exp Med 122:77–82, 1965.)

Germ free pigs and guinea-pigs can develop severe enteritis when removed from the germ-free environment or when contaminated with a single species (Tanami J: J. Chiba Med. Soc. 35:1, 1959; quoted in Luckey T D: Effects of microbes on germ free animals. Adv Appl Microbiol 7:169–223, 1965); (Moberg L J, Sugiyama H: Microbial ecological basis of infant botulism as studied with germfree mice. Infect Immunol 25:653–657, 1979); of note, protection can be afforded by prior seeding with elements of their normal stool flora (Tanami J: J. Chiba Med. Soc. 35:1, 1959; quoted in Luckey T D: Effects of microbes on germ free animals. Adv Appl Microbiol 7:169–223, 1965; Moberg L J, Sugiyama H: Microbial ecological basis of infant botulism as studied with germfree mice. Infect Immunol 25:653–657, 1979.)

"Schaedler's Cocktail," a combination of harmless bacteria, is routinely used in raising specific pathogen-free rodents; without such treatment, the normal physiologic development of the gut does not occur, and the rodents become susceptible to infection with bacteria that would otherwise be considered normal flora for the particular strain of rodent (Harp J A, Chen W, Harmsen A G: Resistance of severe combined immunodeficient mice to infection with Cryptosporidium parvum: the importance of intestinal microflora. Infect Immun 60:3509–3512, 1992.)

Stool Microbial Patterns in NEC

There have been a number of studies of the enteric flora in infants with NEC. Blakely et al. found a decreased percentage of infants with NEC harboring Bacteroides spp. (32% vs 61% in controls) and Lactobacilli (12% vs 48% in controls), and an increased number with C. perfringens (40% vs 13%). (Blakely J L, Lubitz L, Campbell N T, Gillan G L, Bishop R F, Barnes G L: Enteric colonization in sporadic neonatal necrotizing enterocolitis. J Pediatr Gastroenterol Nutr 4:591–595, 1985).

Bell et al. noted increased numbers of Gram (−) bacteria (especially E. Coli and Klebsiella spp.) in infants with NEC. (Bell M J, Feigin R D, Ternberg J L, Brotherton T: Evaluation of gastrointestinal microflora in necrotizing enterocolitis. J Pediatr 92:589–91, 1978).

In contrast, in a prospective case-control study of endemic NEC, we were unable to demonstrate any significant associations between any single aerobic bacterial species and NEC (Gupta S, Morris J G, Panigrahi P, Natero J P, Glass R I, Gewolb I H: Endemic necrotizing enterocolitis:lack of association with a specific infectious agent. Pediatr Infect Dis 13:725–734, 1994).

Lactobacillus/Bifidobacterial Therapy

Fuller has described the utility of live microbial feed supplement which can beneficially affect the host animal by improving its microbial balance (Fuller R: Probiotics in man and animals. J Applied Bacteriol 66:365–378, 1989; Fuller R: Probiotics in human medicine. Gut 32:439–442, 1991.)

There are a number of lines of evidence pointing to the potential benefits of such a therapy (Fuller R: Probiotics in human medicine. Gut 32:439–442, 1991.)

Our studies on the gut ecology of preterm infants with and without NEC, has demonstrated with compelling evidence that only certain Gram (+) organisms that are capable of abrogating the adherence of Gram (−) bacteria can be utilized to block NEC-like disease in rabbit ileal loops (Panigrahi P, Gupta S, Gewolb I H, Morris J G: Occurrence of necrotizing enterocolitis may be dependent on patterns of bacterial adherence and intestinal colonization: Studies in Caco-2 tissue culture and weanling rabbit models. Pediatr Res 36:115–121, 1994.)

A variety of in vitro studies now indicate that intestinal bacteria can inhibit pathogenic bacteria. Sullivan et al. showed that gut isolates of Bifidobacteria, Lactobacilli, Propionibacteria, and Enterococci inhibit C. botulinum in vitro. (Sullivan N M, Mills D C, Riemann H P, Arnon S S: Inhibitions of growth of C. botulinum by intestinal microflora isolated from healthy infants. Microbial Ecology in Health and Disease 1:179–192, 1988). Numerous in vivo studies also lend support to the ability of selected Lactobacilli to modify the intestinal microflora (Conway P: Lactobacilli: Fact and fiction. Ch. 16 in The regulatory and protective role of the normal flora. Grun R, Midvedt T, Norin E, eds. 1988. Stockton Press, pp. 263–281).

For example, seeding the gut with Lactobacilli significantly reduces the numbers of E. Coli in chickens, pigs, and humans. (Fuller R: Epithelial attachment and other factors controlling the colonization of the intestine of the gnotobiotic chicken by lactobacilli. J Applied Bacteriol 45:389–395, 1978; Barrow P A, Brooker B E, Fuller R, Newport M J: The attachment of bacteria to the gastric epithelium of the pig and its importance in the microbiology of the intestine. J Applied Bacteriol 48:147–154, 1980; Lidbeck A, Gustafsson J-A, Nord, C E: Impact of Lactobacillus acidophilus supplements on the human oropharyngeal and intestinal microflora. Scand J Infect Dis 19:531–537, 1987).

Using the rabbit ileal loop model, both, Foster et al. and Johnson and Calia, showed that Lactinex (a commercial preparation containing L. acidophilus and L. bulgaricus) decreased loop fluid production caused by enterotoxigenic

*E. Coli*. (Foster T L, Winans L, Carski T R: Evaluation of lactobacillus preparation in enterotoxigenic *E. Coli*-induced rabbit ileal loop reactions. Am J Gastroenterol 73:238–243, 1980; Johnson D E, Calia F M: The effect of Lactinex on rabbit ileal loop reactions induced by enterotoxigenic Escherichia coli. Curr Microbiol 2:207–210, 1979).

An adherent strain of *Bifidobacterium bifidum* has also been used to mediate the clinical course of rotavirus diarrhea in mice (Duffy L C, Zielezny M A, Riepenhoff-Talty M, Dryja D, Sayahtaheri-Altaie S, Griffiths E, Ruffin D, Barrett H, Rossman J, Ogra P L: Effectiveness of Bifidobacterium bifidum in mediating the clinical course of murine rotavirus diarrhea. Pediatr Res 35:690–695.)

Although these preparations have been used all over the world for decades, more so in European, Scandinavian, and Asian countries, their use has been more empiric than with specific scientific rationale. In turn, large and sometimes contradictory results have been reported on the use of Lactobacilli to treat diarrhea in older children and adults. The selection of Lactobacillus/Bifidobacteria strains have been random without any understanding of their inherent characteristics, and without concurrent consideration of the pathogenesis of the disease in which it is being used.

Effect of Lactobacillus/Bifidobacteria on Neonatal Gut Flora

There have been a limited number of attempts to modify the gastrointestinal flora in the neonatal period. In a double-blind clinical trial with 30 preterm infants (mean weight 1350 gm), Reuman et al. studied the effect of introducing 12 hr oral feedings of $10^9$ *Lactobacillus acidophilus* within 72 hours of delivery. Stool was cultured weekly for Lactobacilli, for Gram (−) bacteria, and for antibiotic resistance of the Gram (−) bacteria. (Reuman P D, Duckworth D H, Smith K L, Kagan R, Ayoub E M: Lack of effect of Lactobacillus on gastrointestinal bacterial colonization in premature infants. Pediatr Infect Dis 5:663–668, 1986).

Lactobacilli were recovered in the stools of 13/15 infants receiving the Lactobacillus supplementation vs 3/15 of the control group. Lactobacilli were also recovered significantly earlier from the treated group (at 19 vs 47 days). No difference was found in the isolation rate of Gram (−) bacteria or in the number of antibiotic-resistant organisms. The details of specific types of Gram (−) organisms were not given, nor was there an attempt to do quantitative cultures.

The choice of *Lactobacillus acidophilus* was arbitrary, and not based on adherence or other characteristics that might determine ability to successfully colonize the intestine (Barrow P A, Brooker B E, Fuller R, Newport M J: The attachment of bacteria to the gastric epithelium of the pig and its importance in the microbiology of the intestine. J Applied Bacteriol 48:147–154, 1980).

However, Mautone et al. have demonstrated a reduction in Gram (−) flora and a percentage increase in Gram (+) bacilli after feeding a suspension containing *Bifidobacterium bifidum* and *Lactobacillus acidophilus* to a group of 77 neonates (61 fullterm; 16 preterm). More recently, Bennett et al. showed that orally administered Bifidobacteria and Lactobacilli could be cultured from the feces of newborn fullterm infants after antibiotic treatment for a number of days after such therapy was discontinued. (Lidbeck A, Gustafsson J-A, Nord, C E: Impact of *Lactobacillus acidophilus* supplements on the human oropharyngeal and intestinal microflora. Scand J Infect Dis 19:531–537, 1987; Bennet R, Nord C E, Zetterstrom R: Transient colonization of the gut of newborn infants by orally administered bifidobacteria and lactobacilli. Acta Paediatr 81:784–787, 1992).

In conclusion, these and other studies indicate that it is possible to successfully modify the gut flora in preterm infants by orally administered Bifidobacteria and Lactobacilli during and after antibiotic therapy. It is almost impossible to avoid using antibiotics in most preterms receiving treatment for other ailments.

We have demonstrated that adherent Gram (−) bacteria are capable of causing NEC-like disease in animal models. We have also shown that it is not the species or strain of bacteria that is responsible for evoking an injury response, rather the microbial ecology (combination of Gram (−) and Gram (+) bacteria) of the premature gut that either protects or gives rise to a cascade of events ultimately resulting in NEC. (Gupta S, Morris J G, Panigrahi P, Natero J P, Glass R I, Gewolb I H: Endemic necrotizing enterocolitis:lack of association with a specific infectious agent. Pediatr Infect Dis 13:725–734, 1994; Panigrahi P, Gupta S, Gewolb I H, Morris J G: Occurrence of necrotizing enterocolitis may be dependent on patterns of bacterial adherence and intestinal colonization: Studies in Caco-2 tissue culture and weanling rabbit models. Pediatr Res 36:115–121, 1994).

The selection of Lactobacillus/Bifidobacteria strains have been random without any understanding of their inherent characteristics, and without concurrent consideration of the pathogenesis of the disease in which it is being used. There is a need in the art for the development of an appropriate strain specifically for premature infants (not full term). The invention described below fulfills this need by providing two specific strains of Lactobacillus which clearly demonstrate reduced tissue injury and reduced acute inflammatory cell infiltration. The present invention is useful in prevention and/or treatment of NEC in premature infants.

SUMMARY OF THE INVENTION

Accordingly, an object of the present invention is to culture Lactobacillus strain(s) in bulk that can be fed to high risk infants via mouth soon after birth to prevent NEC.

A second object is to use the same preparation at a latter point in life to maintain a healthy gut microbial flora and reduce the risk of gastrointestinal (GI) infections.

Yet another object is to use the preparation to prevent or treat other inflammatory mucosal diseases of the GI tract that may have a bacterial etiologic component.

A further object is to use this preparation in fullterms, children and adults, in immuno-compromised patients, patients with cancer and chemotherapy with GI infections, inflammations, and refractory diarrhea after antibiotic therapy.

Another object is to use this preparation to prevent traveler's diarrhea in healthy humans who are traveling abroad and may be exposed to toxic strains of bacteria or viruses.

Another object is to utilize the preparation in animals with disorders of similar nature.

A preferred method of treating gastrointestinal tissue injury includes orally administering Lactobacillus strain, which blocks preterm necrotizing enterocolitis tissue injury as well as necrotizing enterocolitis in fullterm infants. It may also be administered to preterm infants, full-term infants, children and adults and also for treating animals.

Preferably, the Lactobacillus strain is PP 11-34 or PP 11-217. In preferred embodiments, a combination of Lactobacillus strains PP 11-34 and PP 11-217 is administered.

Lactobacillus strain PP 11-34 has been assigned ATCC 202196. Lactobacillus strain PP 11-217 has been assigned ATCC 202195, which are the corresponding deposit accession numbers given by the American Type Culture Collection, 10801 University Boulevard, Manassas, Va. 20110-2209. The depositor is Pinaki Panagrahi, M. D., Ph.D. University of Maryland School of Medicine, whose address is ProBiotix, Inc., Bard Building, Suite 509, 600 East Lombard Street, Baltimore, Md. 21202. The date of deposit was Jan. 19, 1999. The date of the viability test was between Jan. 19, 1999 and Jan. 27, 1999. The viability test was done by the depository. The deposit is capable of reproduction.

PP 11-34, assigned ATCC 202196, is identified as *Lactobacillus salivarius* SS Salivarius PP 11-34.

PP 11-217, assigned ATCC 202195, is identified as *Lactobacillus plantarum* PP 11-217.

The deposit has been made under the Budapest Treaty. During the pendency of this application, access to the invention will be afforded to the Commissioner upon request. All restrictions upon availability to the public will be irrevocably removed upon granting of the patent. The deposit will be maintained in the ATCC Public Depository for a period of thirty years, or five years after the last request, or for the effective life of the patent, whichever is longer. The deposit will be replaced if it should ever become inviable.

A preferred method of treating gastro-intestinal tissue injury comprises orally administering Lactobacillus strain PP 11-34, or PP 11-217, or a combination of the two.

A Lactobacillus strain of the invention prevents gastro-intestinal mucosal infections and bacterial adherence and translocation.

A preferred method of treating diarrhoea comprises orally administering Lactobacillus, which normalizes and/or balances bacterial milieu in gastro-intestinal tracts.

Preferably, the Lactobacillus strain is in lyophilized capsule form. The capsule may be an enteri coated slow-release microcapsule.

The Lactobacillus strain may be administered by means of a naso-gastric tube.

These and further and other objects and features of the invention are apparent in the disclosure, which includes the above and ongoing written specification, with the claims and the drawings.

BRIEF DESCRIPTION OF THE ILLUSTRATIONS

FIGS. 1A, 1B and 1C show the immunofluorescence adherence characteristics of *E. coli* strain 6-1 alone and in combination with two candidate strains of Lactobacillus.

FIGS. 2A, 2B, 2C, and 2D illustrate the gastrointestinal pathology of weanling rabbits.

DETAILED DESCRIPTION OF THE PREFERRED EMBODIMENTS

Figure 1A:
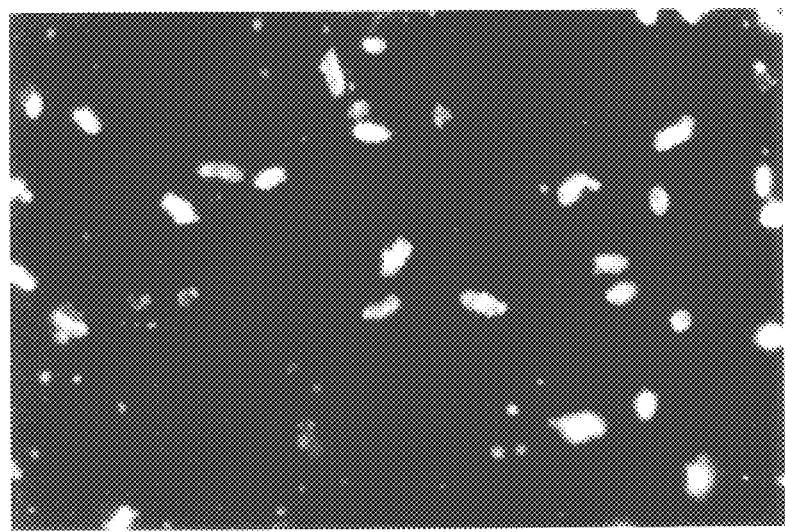

NEC cases cannot be associated with any one infectious agent or with a particular bacterial strain (as characterized by a specific plasmid profile, or previously described virulence factors such as production of delta hemolysin, or β-galactosidase activity (Gupta S, Morris J G, Panigrahi P, Natero J P, Glass R I, Gewolb I H: Endemic necrotizing enterocolitis:lack of association with a specific infectious agent. Pediatr Infect Dis 13:725–734, 1994.) Furthermore, different bacterial species exhibited varying degrees of adherence to Caco-2 cells. Highly adherent *E. coli* strains caused typical NEC-like disease in a weanling rabbit ileal loop model.

We have demonstrated that the stool of preterm infants was characterized by a paucity of aerobic bacterial species: 2.5±1.3 in NEC cases and 2.3±1.0 in controls (Stoll B J, Kanto W P, Glass R I, Nahmias A J, Brann A W: Epidemiology of necrotizing enterocolitis: A case control study. J Pediatr 96:447–451, 1980.)

No Bacteroides or Clostridum spp. were identified. We did not speciate other anaerobic organisms, as the focus of that study was to identify any specific pathogenic agent that could be linked to NEC. However, given our increased interest in identifying potential protective effect of certain strains of bacteria in preventing NEC and in the importance of the total bacterial milieu in predisposing to this complication, we quantitatively analyzed serial stool samples from a group of extremely premature infants for both anaerobic and aerobic bacteria.

In a recent study 29 infants were serially studied of <1000 grams birthweight. Stools were collected at day 10, 20, and 30 of life (all ±2 days). Lactobacilli and Bifidobacteria were only identified in a single infant, consistent with previous findings of decreased Lactobacilli in preterms. The most commonly identified organisms were *K. pneumoniae, E. faecium, S. epidermidis*, and *E. coli*. With the passage of time, the number of different organisms (and total bacterial counts) in stool significantly increased.

These data underscore the paucity of benign organisms in preterm gut, especially in the first month of life. In addition, the fact that only ~3 species of bacteria colonize most preterm infants' guts would presumably allow for overgrowth of potentially pathogenic species (as opposed to a more complex/diverse pattern of colonization). The data thus lend support to our idea of identifying protective organism(s) that could be introduced into the preterm gut early in the postnatal period to afford a measure of protection against the development of NEC. Based on the above data we intended to modify the microbial flora of the preterm intestine in such a way that the deleterious effects of other adherent Gram (–) bacteria will be blocked or minimized.

Two candidate strains of Lactobacilli are described that have been discovered to have the unique property of blocking *E. coli* adherence to cultured cells and NEC-like tissue injury in vivo. These protective characteristics in these strains have been discovered only in two strains out of a total of 87 strains that were isolated from human stools.

As used herein, the term "candidate" refers to the two Lactobacillus strains that show promise in preventing GI disease.

The genus Lactobacillus is not critical to the present invention. However, the inherent properties of only these two strains make them unique in that these two strains block NEC-like disease and other infectious and/or inflammatory disorders of the GI tract.

Figure 1B:
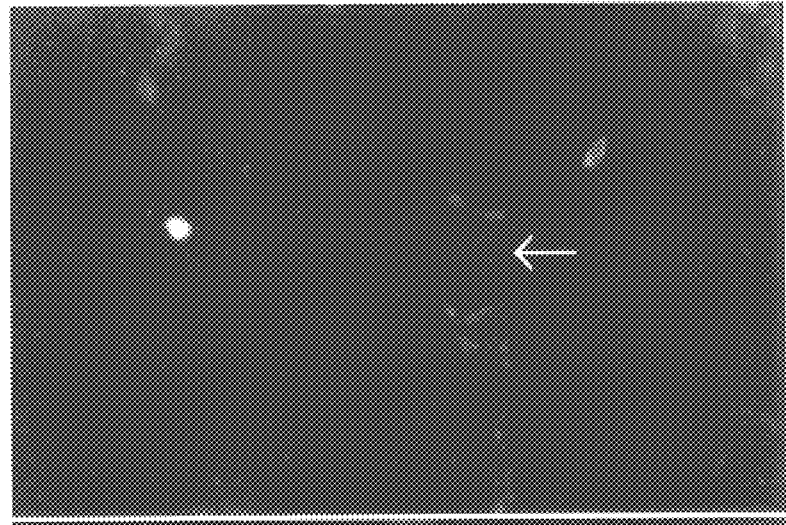
Figure 1C:
Figure 2A:
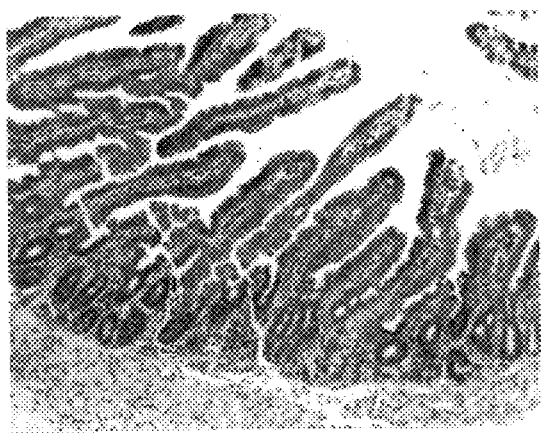
Figure 2B:
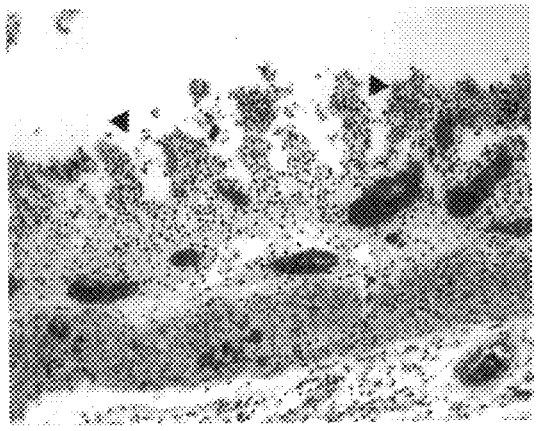
Figure 2C:
Figure 2D:

FIG. 1: shows the immunofluorescence adherence characteristics of *E. coli* strain 6-1 alone and in combination with two candidate strains of Lactobacillus. Adherent *E. coli* are visualized with bright fluorescence. Caco-2 cells and Lactobacilli could be identified in the background with dull staining. Note the total blockage of adherence of *E. coli* during co-infection with Lactobacillus strains PP 11-34 (Panel B) and PP 11-217 (Panel C).

FIG. 2: describes the gastrointestinal pathology of weanling rabbits. The ileal loops were infected with *E. coli* alone and in combination with one of the above strains of Lactobacillus.

2A: Control loop inoculated with PBS: healthy mucosa, with intact simple columnar epithelium, lamina propria, inner circular, and outer longitudinal muscle layers.

2B: Loop infected with E. coli 6-1, note the severe mucosal damage (arrow heads) that extends to deeper muscle layers. There is infiltration of polymorphs and hemorrhage in submucosa and lamina propria.

2C: Loop co-infected with E. coli 6-1 and Lactobacillus PP 11-34.

2D: Loop co-infected with E. coli 6-1 and Lactobacillus PP 11-217. No tissue injury evident other than mild submucosal edema (arrow) and acute inflammatory cell infiltration into the submucosa and lamina propria. Mucosal epithelium, lamina propria, and deeper muscle layers are intact.

Lactobacillus strains have been used for their potential beneficial effects for decades (Conway P: Lactobacilli: Fact and fiction. Ch. 16 in The regulatory and protective role of the normal flora. Grun R, Midvedt T, Norin E, eds. 1988. Stockton Press, pp. 263–281; Fuller R: Epithelial attachment and other factors controlling the colonization of the intestine of the gnotobiotic chicken by lactobacilli. J Applied Bacteriol 45:389–395, 1978.) Starting from yogurt, cultured butter milk, to preparations of similar strains in lyophilized form are available for human use. Each commercial preparation apparently uses their own prototype strain or strain combinations. They are available from various sources including health food stores with the claim that they have beneficial effects. However, the scientific basis or mechanism of action of these preparations have not been described.

Some of the preparations have been shown to have a protective effect in bacterial GI tract infections. To the contrary, controversial findings have been reported using the same preparation in humans (Clements M L, Levine M M and Aaah A J et al. *Lactobacillus prophylaxis* for diarrhea due to enterotoxigenic E. coli. Antimicrob. agents. chemotherap (20):104–108, 1981.)

Lactobacillus strains have not been used in the prevention or treatment of NEC. They have not been used in premature population to treat any medically recognized disease. Our candidate strains on the other hand, are capable of blocking Gram (−) adherence and translocation of Gram (−) bacteria into the deeper layers of the intestine, and in turn, NEC-like disease in vivo.

The rabbit model of NEC has been described in the literature by us and other investigators (Panigrahi P, Gupta S, Gewolb I H, Morris J G: Occurrence of necrotizing enterocolitis may be dependent on patterns of bacterial adherence and intestinal colonization: Studies in Caco-2 tissue culture and weanling rabbit models. Pediatr Res 36:115–121, 1994; Clark D A, Thompson J E, Weiner L B, Schneider A J, Rokahr J E:Necrotizing Enterocolitis:Intramural biochemistry in human neonates & a rabbit model Pediatr Res 19: 919–21, 1985).

However, we were the first to demonstrate a direct causal link between Gram (−) bacterial adherence and subsequent development of NEC. These data indicate that our candidate strains will be able to block the development of NEC in preterm infants if introduced appropriately via nasogastric feeding very early in life before the Gram (−) organisms have a chance to evoke the injury process. It is possible that even after the Gram (−) colonization has set in, our candidate strains minimize the injurious effects caused by the Gram (−) organisms and/or limit the progression of disease beyond that point.

The foregoing and following examples are provided for illustrative purposes only, and are in no way intended to limit the scope of the present invention.

The experiments described herein provide only representative and illustrative data and by no means limit the beneficial use of Lactobacillus in other conditions having similar mechanisms of disease pathogenesis.

EXAMPLE 1

In vitro Immunofluorescence Caco-2 Cell Adherence Studies with E. coli and Lactobacilli Following our previously described protocol we evaluated the adherence potential of 87 Lactobacillus strains in the Caco-2 cell system by monoinfection. Further co-infection studies were conducted using adherent E. coli strain 6-1 combined with different strains of Lactobacillus. A modified staining protocol was developed using immunofluorescence technique to differentiate between E. coli and Lactobacilli following methods similar to one of our previously described procedures (Panigrahi P, Gupta S, Gewolb I H, Morris J G: Occurrence of necrotizing enterocolitis may be dependent on patterns of bacterial adherence and intestinal colonization: Studies in Caco-2 tissue culture and weanling rabbit models. Pediatr Res 36:115–121, 1994; Panigrahi P, Tall B D, Russell R G, DeTolla L J, Morris J G:Development of an in vitro model for study of non-01 Vibrio cholerae virulence using Caco-2 cells. Infect Immun 58: 3415–3424, 1990).

Briefly, mono-and co-infections of Caco-2 cells were performed with Lactobacillus strains ($10^9$ organisms/ml) and E. coli ($10^8$ organisms/ml), followed by washing, fixing with ethyl alcohol, and incubation with hyperimmune rabbit serum against E. coli. After further washings, monolayers were again incubated with FITC-anti-rabbit IgG (Fab specific). Slides were finally washed, dried and examined under epifluorescence. (See FIG. 1).

Caco-2 cell adherence with Lactobacillus strain JPI BL-101 and JPI HS-102, and E. coli 6-1. Note the typical high degree of E. coli adherence in panel "A". Upon co-infection with Lactobacillus PP 11-217, adherence of E. coli is almost completely blocked, only two fluorescent E. coli are seen in the field, with numerous unstained Lactobacilli adhered to Caco-2 cells in the background in panel "B". Similar blockage of E. coli adherence by Lactobacillus PP 11-34 in panel "C".

EXAMPLE 2

E. coli Translocation In Caco-2 Transwell System with Lactobacillus Strains

Caco-2 cells are derived from human adenocarcinoma cells which show all the morphological and functional characteristics of mature small intestinal epithelial cells after differentiation (Panigraph P., Tall B D, Russell R G, DeTolla I J, Morris Jr. J G, Development of an in vitro model for study of non-01 Vibrio cholerae virulence using Caco-2 cells, Infect Immun. 1990; 58:3415–3424; Panigrahi P, Gupta S, Gewolb I H, Morris J G, Occurrence of necrotizing enterocolitis may be dependent on patterns of bacterial adherence and intestinal colonization: studies in Caco-2 tissue culture and weanling rabbit models, Pediatr. Res. 1994; 36:115–121). Fully differentiated (10–12 day old) Caco-2 cells were grown on polycarbonate filters in Transwell clustsers and infected from the apical side (top) with $10^8$ E. coli strain alone or in combination with $10^9$ Lectobacillus strain PP 11-34 or PP 11-217. The basolateral (bottom) medium was plated on L-agar plates for quantitating translocated E. coli at hr 1, 3 and 6. There was a 10–100 fold decrease in E. coli translocation when either of the two Lactobacillus strains were used compared to positive controls where E. coli was used alone.

EXAMPLE 3

In vivo Weanling Rabbit Ileal Loop Studies

Rabbit ileal loop studies were conducted in duplicate loops in duplicate animals. Weanling rabbits between 350–400 gm were used. Surgical and inoculation procedures, essentially identical to our previously described methods were followed (Panigrahi P, Gupta S, Gewolb I H, Morris J G: Occurrence of necrotizing enterocolitis may be dependent on patterns of bacterial adherence and intestinal colonization: Studies in Caco-2 tissue culture and weanling rabbit models. Pediatr Res 36:115–121, 1994.) Lactobacillus strain PP 11-34 and PP 11-217 ($10^9$ organisms/ml) were used as the candidate blocking strain. Two other strains (non-adhering Lactobacillus strains from our collection) were included as negative controls. Non-infected loops inoculated with PBS were maintained in each animal.

Lactobacillus strain PP 11-34 and PP 11-217 ($10^9$ organisms/ml) were able to block tissue damage in the loops. There was minimal fluid accumulation and submucosal edema in these loops. There was typical NEC-like disease in *E. coli* control loops. Although the negative control Lactobacilli were unable to block mucosal damage and further tissue injury, there was some reduction in fluid accumulation compared to the *E. coli* positive control.

Preferably, the present Lactobacillus strains are administered in an approximate range of about $10^8$–$10^{11}$ organisms, at least twice daily. Preferably, about $10^9$ organisms are administered. The strains may each be given separately or in a combination to about $10^9$ organisms. The strains may be provided in lyophilized form, reconstituted in a vehicle or in capsule form. Capsules may be coated and in the form of acid-resistant slow-release microcapsules. Administration may be orally or via a naso-gastric tube. It can be delivered into the intestine via mouth, naso-gastric tube, jejunal tube, colorectal enema, or any other method appropriate for the diseased state of the patient. It may be delivered in any other biocompatible carrier.

While the invention has been described with reference to specific embodiments, modifications and variations of the invention may be constructed without departing from the scope of the invention, which is defined in the following claims.

We claim:

1. A method of preventing neonatal necrotizing enterocolitis gastro-intestinal tissue injury comprising naso-gastrically administering *Lactobacillus salivarius* strain ATCC 202196 to preterm infants.

2. A method of preventing neonatal necrotizing enterocolitis gastro-intestinal tissue injury comprising naso-gastrically administering *Lactobacillus plantarum* strain ATCC 202195 to preterm infants.

3. A method of preventing neonatal necrotizing enterocolitis gastro-intestinal tissue injury comprising naso-gastrically administering *Lactobacillus salivarius* strain ATCC 202196 and *Lactobacillus plantarum* strain ATCC 202195 to preterm infants.

4. A method of preventing preterm neonatal necrotizing enterocolitis gastro-intestinal mucosal infections comprising naso-gastrically administering a Lactobacillus strain selected from the group consisting of *Lactobacillus salivarius* ATCC 202196, *Lactobacillus plantarum* ATCC 202195 and combinations thereof, for blocking bacteria before tissue damage occurs.

5. A biologically purified Lactobacillus strain selected from the group consisting of *Lactobacillus salivarius* ATCC 202196, *Lactobacillus plantarum* ATCC 202195 and combinations thereof, for apical administration to treat mucosal tissue in preterm infants before injury is caused by infection and inflammation.

6. The Lactobacillus strain of claim 5, wherein the Lactobacillus strain is in lyophilized capsule form.

7. The Lactobacillus strain of claim 6, wherein the capsule is a coated acid-resistant slow-release microcapsule.

8. A method of preventing preterm neonatal gastro-intestinal tissue injury comprising naso-gastrically administering *Lactobacillus salivarius* strain ATCC 202196, *Lactobacillus plantarum* strain ATCC 202195, or combinations thereof twice daily in dosages of about $10^8$ to $10^{11}$ microorganisms per ml to preterm infants and thereby preventing preterm neonatal gastro-intestinal tissue injury.

9. A method of preventing necrotizing enterocolitis (NEC) in preterm neonatal infants comprising naso-gastrically feeding *Lactobacillus salivarius* strain ATCC 202196, *Lactobacillus plantarum* strain ATCC 202195, or combinations thereof twice daily in dosages of about $10^8$ to $10^{11}$ microorganisms per ml to preterm infants for preventing neonatal necrotizing enterocolitis.

10. The method of claim 9, wherein bacterial translocation is prevented.

11. A liquid product for preventing preterm neonatal necrotizing enterocolitis gastro-intestinal injury comprising a Lactobacillus strain selected from the group consisting of *Lactobacillus salivarius* ATCC 202196, *Lactobacillus plantarum* ATCC 202195 and combinations thereof, in ml doses having about $10^8$ to $10^{11}$ microorganisms per ml for naso-gastric feeding to preterm infants before tissue injury for preventing preterm neonatal necrotizing enterocolitis gastro-intestinal injury.

12. A product for preventing preterm neonatal necrotizing enterocolitis gastro-intestinal injury comprising *Lactobacillus salivarius* strain ATCC 202196, *Lactobacillus plantarum* strain ATCC 202195, or combinations thereof in ml doses having about $10^8$ to $10^{11}$ microorganisms per ml provided in lyophilized form, reconstituted in a vehicle or in coated capsules in the form of acid-resistant slow release microcapsules for naso-gastric feeding to preterm infants before tissue injury for preventing preterm neonatal neonatal necrotizing enterocolitis gastro-intestinal injury.

* * * * *